(12) United States Patent
Stone

(10) Patent No.: US 7,112,633 B2
(45) Date of Patent: Sep. 26, 2006

(54) PREPARATION OF A COMPOUND CONTAINING CYCLIC AND LINEAR CARBONATE GROUPS

(75) Inventor: Vincent Stone, Brussels (BE)

(73) Assignee: Surface Specialties, S.A., Brussels (BE)

( * ) Notice: Subject to any disclaimer, the term of this patent is extended or adjusted under 35 U.S.C. 154(b) by 239 days.

(21) Appl. No.: 10/486,733

(22) PCT Filed: Aug. 5, 2002

(86) PCT No.: PCT/EP02/08723

§ 371 (c)(1),
(2), (4) Date: Feb. 13, 2004

(87) PCT Pub. No.: WO03/016298

PCT Pub. Date: Feb. 27, 2003

(65) Prior Publication Data

US 2004/0198991 A1    Oct. 7, 2004

(30) Foreign Application Priority Data

Aug. 17, 2001  (EP) .................................... 0119912

(51) Int. Cl.
*C08F 263/00*   (2006.01)
*C08F 18/12*    (2006.01)
*C07D 317/10*   (2006.01)
*C07D 493/00*   (2006.01)

(52) U.S. Cl. ...................... 525/277; 525/242; 526/269; 526/270; 526/271; 526/272; 558/260; 549/228; 549/229; 549/230

(58) Field of Classification Search ................ 522/162, 522/163, 169, 168, 183, 182; 525/242, 277; 558/260; 526/269, 270, 271, 272; 549/228, 549/229, 230

See application file for complete search history.

(56) References Cited

U.S. PATENT DOCUMENTS

| | | |
|---|---|---|
| 2,979,514 A | 4/1961 | Beavers et al. |
| 3,225,008 A | 12/1965 | D Alelio |
| 4,423,235 A | 12/1983 | Burgard et al. |
| 5,047,261 A | 9/1991 | Moussa et al. |
| 5,658,989 A | 8/1997 | Nakano et al. |
| 5,763,622 A | 6/1998 | Podszun et al. |
| 6,001,535 A | 12/1999 | Podszun et al. |

OTHER PUBLICATIONS

Couvret, D. et al., European Polymer Journal, vol. 27, No. 2, p. 193-197 (1991).

*Primary Examiner*—Sanza L. McClendon
(74) *Attorney, Agent, or Firm*—Wenderoth, Lind & Ponack, L.L.P.

(57) ABSTRACT

The invention relates to a process for the preparation of compound(s) comprising at least one acrylate or methacrylate group, at least one linear carbonate group and at least one 5-membered cyclic carbonate group. The process comprises (A) a selective ring-opening step and (B) a (meth) acrylation step. The process is environment-friendly and compounds obtained are usable in radiation curable compositions, for example in radiation-curable inks.

15 Claims, No Drawings

PREPARATION OF A COMPOUND CONTAINING CYCLIC AND LINEAR CARBONATE GROUPS

The present invention relates to a process for the preparation of a compound comprising at least one acrylate or methacrylate group, at least one linear carbonate group and at least one 5-membered cyclic carbonate group. The invention also relates to uses of such compounds.

Compounds comprising an acrylate or methacrylate group, a linear carbonate group and a 5-membered cyclic carbonate group are known to be used in radiation curable compositions. Compositions curable by ultraviolet rays or by accelerated electron beam have found a wide range of applications in numerous fields, for example, as coatings, varnishes and paints for protecting and decorating the most diverse substrates such as glass, metals, plastics, paper, as printing varnishes and inks curable by ultraviolet rays or as adhesives for laminates, and the like.

Compared with heat curable compositions, radiation curable compositions have many advantages. These compositions do not contain solvents, contrary to the thermosetting compositions, because their constituents are selected so that they all polymerize almost completely during curing; in this way, an important source of environmental pollution is eliminated. Next, radiation curing requires less energy than the heat required to evaporate the solvents and to cure thermosetting compositions, which represents a significant saving of energy; this mode of curing also has the advantage that it can be performed at low temperature, and thus allows the coating of heat sensitive substrates. Furthermore, in many applications, radiation curable compositions allow to work at very high production rates and continuously, because these compositions cure in less than a few seconds, which is not the case for heat curable compositions. Moreover, these radiation curable compositions often allow to obtain performances that other types of compositions do not allow to achieve.

Compositions curing through radiation-initiated radical polymerization generally contain at least one of the 3 following reactive components:

1°) one or more radiation polymerizable reactive oligomers or prepolymers, the molecular weight of which is generally lower than 10,000 and which have, at the chains ends or laterally along the chain, acrylic, methacrylic, vinyl or allyl groups.

2°) one or more polyethylenically unsaturated reactive monomers which contain at least two ethylenically unsaturated groups. These reactive monomers are preferably diacrylates or polyacrylates of polyols of low molecular weight. The essential role of these reactive monomers is to enable to adjust the viscosity depending on the intended industrial application.

3°) one or more monoethylenically unsaturated reactive monomers which contain only one ethylenically unsaturated group per molecule. Examples of such monomers are the monoacrylates or monomethacrylates of monohydric or polyhydric aliphatic alcohols. Other examples of such monomers are styrene, vinyl-toluene, vinyl-acetate, N-vinyl-2-pyrrolidone, N-vinylpyridine, N-vinylcarbazole, and the like. These monomers are added to the compositions as reactive diluents in order to lower the viscosity. These monomers can also have a considerable influence on the physical and chemical properties of the final coatings obtained. The reactive monomers used in the radiation curable compositions should have the following properties low toxicity low volatility and odour low viscosity high reactivity.

However, current commercially available systems never completely fulfill these prerequisites at the same time. Compromise must be made since in general, with these systems, the lower the viscosity of the monomer, the lower the reactivity of the formulation at a given monomer content and the lower the viscosity of the monomer, the higher the volatility and the lower the human olfactory threshold.

Besides the above-mentioned reactive components, the radiation curable compositions may eventually contain various auxiliary constituents to adapt them to their specific technical applications. Optionally, a photoinitiator generally associated with a tertiary amine is added to the composition so that, under the influence of ultraviolet irradiation, the photoinitiator produces free radicals which initiate the crosslinking (curing) of the composition. The photoinitiator is, for example, benzophenone, benzil dimethylketal, thioxanthones, and the like.

European Patent Application EP 0 406 057 describes a radiation curable composition comprising a carbonate (meth)acrylic compound of general formula:

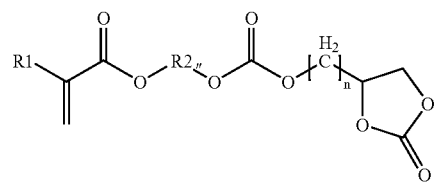

wherein R1=H or CH3, R2=alkylene or alkylene ether chain with 2 to 6 C atoms, $1 \leq n \leq 6$. It is explained in the document that these low viscous compounds are useful as reactive diluent in radiation curable compositions, permitting to obtain markedly superior radiocrosslinking rates. EP 0 406 057 explains that this very high reactivity of the compounds and of the corresponding radiocrosslinkable composition towards radiation makes it possible to reduce the quantity of initiator when photocrosslinking is employed in the presence of an initiator, while keeping to very short exposure periods. This saving in initiator is appreciable in the case of use of systems such as benzophenone/tertiary amine or thioxanthone/tertiary amine, because it makes possible to reduce considerably the proportion of amine required. Now, it is known that the presence of an amine, apart from the fact that the odour is unpleasant, results in yellowing and a considerable decrease in the hardness of the coating.

According to EP 0 406 057, the carbonate (meth)acrylic compound is synthesized by a two steps process:

1/Synthesis of the chloroformic acid ester of formula:

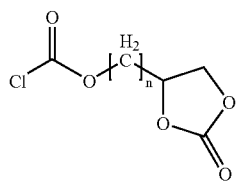

by complete phosgenation of the corresponding triol:

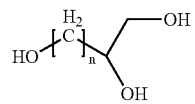

(EP 0 406 057 mentions that the triol itself is prepared by a known process such as the one described in U.S. Pat. No. 2,446,145.

2/Reaction of the chloroformic acid ester with a hydroxyalkyl(meth)acrylate at 0° C. in dichloromethane:

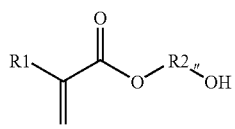

However such process have drawbacks, which are mainly the following:

use of phosgene in step 1, a highly toxic substance that can be only used through expensive secured equipments and safety procedures.

generation of corrosive HCl that leads to the need to work below room temperature during step 2. HCl is neutralized by a tertiary amine for example pyridine added dropwise with the reaction temperature maintained below 5° C.

U.S. Pat. No. 6,001,535 describes multi(meth)acrylate compounds of the formula (A), which are suitable for the production of photosensitive recording materials, for example for the production of offset printing plates. The multi(meth)acrylate compounds are of the formula (A):

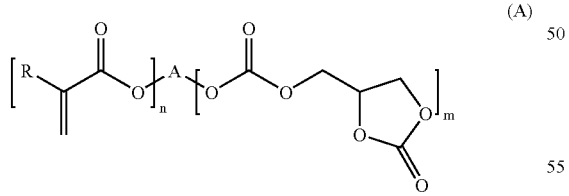

in which R=H or CH3, $1 \leq n \leq 5$, $1 \leq m \leq 3$ providing that n+m is at least 3, A=(n+m)–valent hydrocarbon residue with 3 to 30 C atoms, which may be OH-substituted and may contain up to 8 ether bridges.

U.S. Pat. No. 6,001,535 explain that the compounds can be obtained by reacting polyhydroxy compounds with chloroformic acid and (meth)acrylic acid chloride. The chloroformic acid ester and its process of preparation are mainly the same as described in EP 0 406 057. Thus, there remains a need to develop compounds usable in radiation curable compositions through environment-friendly raw materials and process.

The present invention accordingly provides a new process for the preparation of compound(s) comprising at least one acrylate or methacrylate group, at least one linear carbonate group and at least one 5-membered cyclic carbonate group characterized in that it comprises steps (A) and (B) defined below.

Step (A) is a selective ring-opening step in which a compound of general formula (I):

wherein:

R2 represents a bivalent alkylene radical: $-(CR3R4)_p-$ with p>3,

R3 and R4 being independently chosen from: hydrogen, cycloaliphatic radical, aromatic radical, alkyl, alkylene or alkenylene C1–C10 chain which chain is linear or branched, contains from 0 to 8 ether bridges, and R3 and/or R4 may be substituted by alkyl or alkenyl group, provided that R3 and R4 are free of reacting hydroxyl group, is reacted with a 5-membered cyclic carbonate group compound of general formula (II):

wherein:

R5 represents a bivalent alkylene radical: $-(CR6R7-CR8R9)-$,

R6, R7, R8 and R9 being independently chosen from: hydrogen, cycloaliphatic radical, aromatic radical, alkyl, alkylene or alkenylene C1–C10 chain which chain is linear or branched, contains from 0 to 8 ether bridges, and R6 and/or R7 and/or R8 and/or R9 may be substituted by an alkyl, alkenyl, hydroxyl group(s), or other 5-membered cyclic carbonate group of formula (II), provided that at least one of R6, R7, R8, R9 is substituted by a reacting hydroxyl group.

Step (B) is an acrylation step in which the compound obtained in the selective ring-opening step (A) is reacted with acrylic acid, methacrylic acid, acrylate ester, methacrylate ester, or oligomer(s) thereof to form a compound of general formula (III):

wherein:

R10 represents a bivalent alkylene radical: —(CR11R12—CR13R14)—, with:

R11, R12, R13 and R14 being, respectively, identical to R6, R7, R8 and R9 if the latter were not substituted with reacting hydroxyl group and the hydroxyl-substituent of R6, R7, R8 or R9 is at least partly replaced by the moiety

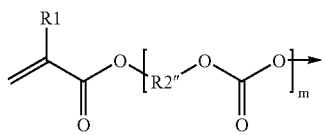

wherein:

R1=hydrogen or methyl, and $1 \leq m \leq 10$, the arrow denotes the point of attachment to R11, R12, R13 or R14.

When p=3 in the above-defined formula (I), the compound (I) is a 6-membered cyclic carbonate. The compound (I) may contain more than 6 members in its cycle, as is the case in the formula (I) when p is greater than 3. In the following description, compound (I) will be generally referred to as "6-membered cyclic carbonate". However this is only for the sake of clarity and does not mean that the present invention is limited to a process wherein compound (I) is necessarily a 6-membered cyclic carbonate.

The compound defined in the above formula (II) is often referred to in the following description as "the "5-membered cyclic carbonate". The process of the present invention makes use of an alternative chemistry that allows using cheap and safe raw materials. This process permits to avoid not only the use of highly toxic phosgene but also the generation of corrosive hydrochloric acid. No special equipment is required and generation of valueless by-products is reduced, which makes the whole process inexpensive.

Literature exists for ring-opening reactions with alcohols. Ring opening of 5-membered cyclic carbonates is for example described in: E. I. Stout, W. M. Dane, K. E. Kolb, J. Org. Chem., 36, 3126 (1971). U.S. Pat. No. 5,466,754 describes ring opening of 6-membered cyclic carbonate.

As both 5-membered and 6-membered cyclic carbonates are reported to be able to be opened by an hydroxyl group, one would think that both rings would be opened during the reaction step (A). This would lead to a mixture containing a lot of different reaction products requiring further time- and cost-consuming separation steps.

The applicant has surprisingly discovered that ring compounds (I) and (II) may react together in a selective way so that the ring of compound (I) may be opened by the hydroxyl group(s) of the 5-membered ring compound (II) while leaving the 5-membered ring compound (II) intact.

The applicant has discovered that a selective reaction may be obtained when compound (I) is free of hydroxyl reacting group. Compound (I) may contain hydroxyl groups not accessible to reaction, for example because of steric hindrance. However, preferably, compound (I) is free of any hydroxyl group to favour selectivity of the reaction (A). The applicant has discovered that the position of the (at least one) hydroxyl group in compound (II) is an important factor for the sought-after selectivity. At least one of the carbon atoms of the 5-membered cycle bears a substituent which itself bears at least one hydroxyl group. Thus the hydroxyl group is in an alpha position of the cycle or farther. In order to lead to selective and efficient reaction, it is preferred that the hydroxyl group is on a primary or secondary carbon. Most preferably, the hydroxyl group(s)s is/(are) present in methylol groups. It was observed that the presence of a methylol group on the 5-membered cyclic carbonate compound (II) may be particularly favourable to selectivity and speed of the reaction (A).

The selective ring-opening step of the process, i.e. step (A) generates a distribution of ring-opened adducts of varying lengths:

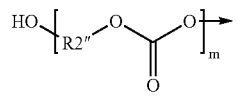

wherein:

$1 \leq m \leq m_{max}$.

The distribution and $m_{max}$ can be adapted by playing on the stoichiometry of the starting reagents. When a 1:1 eq:eq stoichiometry is used, the monomer-

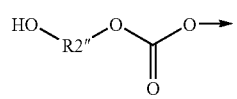

and dimer-adducts,

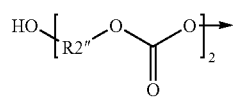

may represent more than 40% and 30% of the distribution (as measured by HPLC). The higher the excess in cyclic carbonate compound (I), the higher $m_{max}$.

More preferably, the stoichiometry is adapted such as $m_{max}$ is equal to 10. An opened adduct of such maximum length is easily workable, for example in a polymerization process. In order to promote reaction speed and to achieve quantitative conversion of the cyclic carbonate compound (I) while leaving the 5-membered cyclic groups of compound (II) intact, working step (A) in presence of a catalyst is preferred.

Catalysts that may be used are, for example:

Brönstedt acids such as hydrogen halides (HF, HBr, HCl), sulfonic acids (in particular para-toluenesulfonic acid, methane sulfonic acid, dodecyl benzene sulfonic acid, trifluoromethane sulfonic acid, naphtalene sulfonic acid), trifluoroacetic acid, sulfuric acid.

Acidic cation-exchange resins: AMBERLYST 15 (from Röhm and Haas).

Brönstedt bases such astriethylamine, tetramethyl guanidine, 1,4-diazabicyclo[2.2.2]octane.

Lewis acids: metal halides (monobutyltin trichloride, dibutyltin dichloride, tributyltin monochloride, tributyltin monofluoride, stannous chloride, stannous bromide, stannous iodide, aluminium chloride, titanium chloride, antimony pentachloride), metal oxides (dibutyltin oxide, hydroxybutyltin oxide, dibutyltin dimethoxide.) or metal carboxylates (dibutyltin dilaurate, butyltin trisoctoate, stannous oleate, stannous dioctoate.)

Onium salts: ammonium salt, sulfonium salt, phosphonium salt or iodonium salt whose cations come from a metal halide (N,N-dimethyl-N-benzyl anilinium antimony hexafluoride, triphenyl sulfonium boron tetrafluoride, ethyltriphenyl phosphonium antimony, duiphenyl iodonium arsenic hexafluoride) or a. Brönstedt acid (pyridinium p-toluene sulfonate).

More preferably the catalyst is chosen such as being active also for step (B). This permits to avoid a lengthy and waste-generating step of washing the catalyst before acrylation. If the acrylation is made by direct esterification with (meth)acrylic acid and/or oligomers thereof, the catalyst is more preferably a. Brönstedt acid, an acidic cation-exchange resin, or a Lewis acid, more preferably a. Brönstedt acid, more preferably a sulfonic acid, more preferably para-toluenesulfonic acid.

If the acrylation is made by transesterification with (meth) acrylate ester, the catalyst is more preferably a. Lewis acid, more preferably a metal carboxylate, more preferably butyltin trisoctoate (FASCAT 4102 from Atofina).

Preferably, the catalyst concentration is comprised between 0.05 and 5% by weight of the reacting mixture. Higher concentration would not allow good ring opening selectivity as well as avoiding side reactions such as decarboxylation. Lower concentration would not allow reaction times affordable at industrial scale.

Use of solvent during the first step is optional. More preferably, no solvent is used. A solvent may however be found useful to reduce the viscosity of the reaction mixture and thus allow a better spatial homogeneity of the reaction temperature. It may also be used to improve the solubility of the catalyst in the reaction mixture. If a solvent is to be used, it must be aprotic so as avoiding any interference with the ring opening reaction. It can be an aromatic hydrocarbon (such as toluene.), an aliphatic hydrocarbon (for example heptane), an ester (for example butyl acetate), a ketone (for example acetone, methyl isobutyl ketone), an halogenated hydrocarbon (for example dichloromethane.), an ether (for example tetrahydrofuran)

More preferably the solvent should be the same as used in step 2, if any, so as to avoid distillation and stripping of the latter by the second step. Preferably, the solvent is toluene. If a solvent has to be used, it should be used in amount between 5 and 80% by weight of the reacting mixture, preferably between 10 and 50% by weight of the reacting mixture. Lower concentration would not decrease significantly the viscosity. Higher concentration would make the reaction unacceptably slow.

Preferably, the reaction temperature during step (A) is comprised between 20 and 150° C., more preferably between 40 and 100° C. Such reaction temperature ranges were found to be low enough to ensure good ring opening selectivity as well as avoiding side reaction (e.g. decarboxylation) and high enough to allow reaction times affordable at industrial scale. Completion of the first step is determined by the complete disappearance of the compound of formula (I). The presence of the latter may be determined by well-known methods such as for example Thin Layer Chromatography, NMR.

Preferably, R3 and/or R4 is chosen among hydrogen, methyl, ethyl, propyl, isopropyl, n-butyl, sec-butyl, tert-butyl, 2-butenyl, 3-butenyl, 2-pentenyl, 3-pentenyl, 4-pentenyl, phenyl or benzyl.

Preferably, p=3. In this case, compound (I) is a 6-membered cyclic carbonate compound. It was found that the reaction of such a 6-membered cyclic carbonate compound (I) with a 5-membered cyclic carbonate group compound of general formula (II) is highly selective and may lead to useful reaction products.

Preferably, compound (I) is:

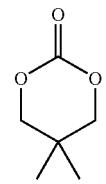

neopentylglycol carbonate

As described in Sarel, S.; Pohoryles, L. A., *J. Am. Chem. Soc.* 1958, 80, 4596, the latter may be prepared, for example, by distillative transesterification of neopentyl glycol with diethyl carbonate.

Preferably, compound (II) is:

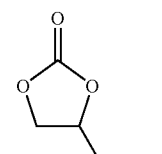

glycerine carbonate

As described in EP 0 739 888, the latter may be, for example, obtained by carbonation of glycerol in the presence of ethylene carbonate.

In another preferred embodiment, compound (II) is:

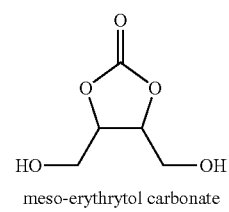

meso-erythrytol carbonate

The latter may be, prepared by epoxidation of 2-butene-1, 4-diol treating the latter with an organic hydroperoxide as described, for example, in EP 0 308 188, followed by reaction of the epoxide groups with carbon dioxide, using a process described in U.S. Pat. No. 4,892,954.

In a third preferred embodiment of the invention, compound (II) is:

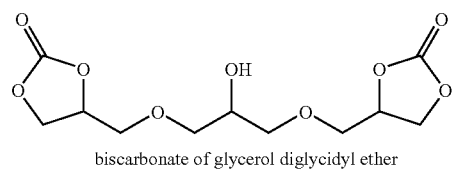

biscarbonate of glycerol diglycidyl ether

The latter may be, for example, prepared by reaction of the epoxide groups of glycerol diglycidyl ether with carbon dioxide, using a process described in U.S. Pat. No. 4,892, 954.

The reaction products obtained when such preferred compounds are used are detailed on the enclosed table:

Preferably, compounds obtained by the process according to the invention are used in a radiation-curable ink, particularly in ink jet applications. For example compositions comprising compounds prepared by the process according to the invention may be prepared for use as printing ink for printing substrates such as paper, cardboard, glass, metal,

| (I) | (II) | (Meth)acrylate (III) |
|---|---|---|
| 1. neopentyl-glycol carbonate | glycerine carbonate | |
| 2. neopentyl-glycol carbonate | meso-erythrytol carbonate | |
| 3. neopentyl-glycol carbonate | biscarbonate of glycerol diglycidyl ether | |

Compounds obtained by the process according the invention can be used in a radiation curable composition. Indeed the compounds produced by the process according to the present invention can be highly reactive to radiation-initiated radical polymerisation. When photopolymerisation is made in the presence of an initiator, low quantities of initiator can be used thanks to this high reactivity. This saving in initiator is appreciable since the latter generally induces

- an increase of the overall cost of the formulation (photoinitiator is in general the most expensive component).
- the presence of odors and migratables originating from the photoinitiator itself or its photolysis products in the UV-cured coatings.
- a reduction of the maximum film thickness that can be cured (filtering effect).
- a lower durability of the UV formulation.
- an increased photoyellowing during and after cure.

plastics and artificial leathers and for printing bottles made from polyethylene, polypropylene. In other embodiments, compositions comprising compounds prepared by the process according to the invention are used for industrial coatings.

EXAMPLE 1

Step (A): Preparation of the Carbonate-Adduct 124.3 g (1 mol OH) of glycerine carbonate (GC) sold by Ube Industries Ltd., 132.9 g (0.95 equivalent) of 4,4-dimethyl trimethylene carbonate, also called neopentyl glycol carbonate, (DMTMC, 93% pure according to $^1$H NMR) available from Ube Industries Ltd., and 2.6 g (1% by weight of the reacting mixture) p-toluenesulfonic acid (PTSA), are charged in a double-wall glass reactor with a capacity of 0.5 l and fitted with an agitator, a thermometer, a gas inlet tube, a connection to vacuum and an azeotropic distillation column.

The mixture is heated to 40° C. and stirred for 3 h, a reaction time found long enough by Thin Layer Chromatography and $^1$H NMR for complete disappearance of the DMTMC. Titration measurements showed no evolution for the concentration in OH groups, indicating that no significant decarboxylation occurs.

Step (B): Preparation of the Acrylate Compound

Direct esterification of the carbonate adduct was carried out adding to the reaction mixture of Ste (A), 76.3 g (1.1 mol) acrylic acid, 229.2 g toluene (40% by weight of the reacting mixture), and 1000 ppm methyl ether hydroquinone (MeHQ).

Additional PTSA (6 g) is also added to reach an end concentration of 1.5% by weight of the reacting mixture.

Oxygen is injected to prevent gelling.

The mixture is heated to reflux (about 110° C.) and stirred until no more water is distilled over. When no more water is distilled over, the mixture is cooled to 60° C. and toluene (587 g) added to reach an end concentration of 50% toluene.

This mixture is washed three times with 20% by weight of the reacting mixture water containing 20% NaCl, dried via azeotropic distillation to remove all the water and finally filtered.

The toluene was distilled and stripped under high vacuum (30 mmHg) to remove all traces of toluene.

Production of Coating by Photocrosslinking of Acrylate Compound 100 parts by weight of the acrylate compound is mixed with 5 parts by weight of photoinitiator.

The photoinitiator employed is IRGACURE 651, which is a marketed by Ciba (2,2-dimethoxy-2-phenylacetophenone).

The composition is then applied onto paper with the aid of straight edge calibrated to form a uniform film 10 microns in thickness.

The composition thus applied is then irradiated with an UV source consisting of a medium-pressure mercury vapour lamp with a power of 120 W/cm, whose radiation is concentrated with the aid of a semi-elliptical reflector. The degree of conversion of acrylate compound is higher than 80% after 1 s of irradiation.

By way of comparison, tripropylene glycol diacrylate (TPGDA) has a degree of conversion of less than 60% under the same conditions.

The invention claimed is:

1. Process for the preparation of a compound comprising at least one acrylate or methacrylate group, at least one linear carbonate group and at least one 5-membered cyclic carbonate group characterized in that it comprises:
   (A) a ring-opening step in which a compound of general formula (I):

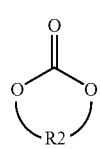

(I)

wherein:
R2 represents a bivalent alkylene radical: —(CR3R4)$_p$— with p≧3,
R3 and R4 being independently chosen from: hydrogen, cycloaliphatic radical, aromatic radical, alkyl, alkylene or alkenylene C1–C10 chain which chain is linear or branched, contains from 0 to 8 ether bridges, and R3 and/or
R4 may be substituted by alkyl or alkenyl group,
provided that R3 and R4 are free of reacting hydroxyl group,
is reacted with a 5-membered cyclic carbonate group compound of general formula (II):

(II)

wherein:
R5 represents a bivalent alkylene radical: —(CR6R7—CR8R9)—,
R6, R7, R8 and R9 being independently chosen from: hydrogen, cycloaliphatic radical, aromatic radical, alkyl, alkylene or alkenylene C1–C10 chain which chain is linear or branched, contains from 0 to 8 ether bridges,
and R6 and/or R7 and/or R8 and/or R9 may be substituted by an alkyl, alkenyl, hydroxyl group(s), or other 5-membered cyclic carbonate group of formula (II),
provided that at least one of R6, R7, R8, R9 is substituted by an hydroxyl group
and (B) an acrylation step in which the compound obtained in the ring-opening step (A) is reacted with acrylic acid, methacrylic acid, acrylate ester, methacrylate ester, or oligomer(s) thereof to form a compound of general formula (III):

(III)

wherein:
R10 represents a bivalent alkylene radical: —(CR11R12—CR13R14)—, with:
R11, R12, R13 and R14 being, respectively, identical to R6, R7, R8 and R9 if the latter were not substituted with hydroxyl group an at least a part of the hydroxyl-substituent of R6, R7, R8 or R9 is replaced by the moiety

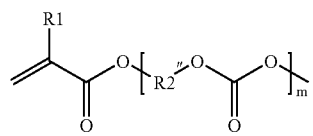

wherein:

R1=hydrogen or methyl, and $1 \leq m \leq 10$.

2. Process according to claim 1, wherein step (A) is made in presence of a catalyst.

3. Process according to claim 2, wherein the catalyst is a sulfonic acid, preferably para-toluenesulfonic acid.

4. Process according to claim 2, wherein the catalyst is a metal carboxylate, preferably butyltintrisocoate.

5. Process according to claim 2, wherein the catalyst concentration is comprised between 0.05 and 5% by weight of the reacting mixture.

6. Process according to claim 1 wherein the reaction temperature during step (A) is comprised between 20 and 150° C.

7. Process according to claim 6 wherein the reaction temperature during step (A) is comprised between 40 and 100° C.

8. Process according to claim 1 wherein R3 and/or R4 is chosen among hydrogen, methyl, ethyl, propyl, isopropyl, n-butyl, sec-butyl, tert-butyl, 2-butenyl, 3-butenyl, 2-pentenyl, 3-pentenyl, 4-pentenyl, phenyl or benzyl.

9. Process according to claim 1 wherein the hydroxyl group in compound (II) is a methylol group.

10. Process according to claim 1 wherein p=3.

11. Process according to claim 1 wherein compound (I) is:

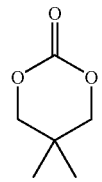

neopentylglycol carbonate.

12. Process according to claim 1 wherein compound (II) is:

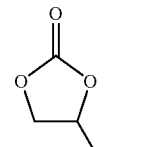

glycerine carbonate.

13. Process according to claim 1 wherein compound (II) is:

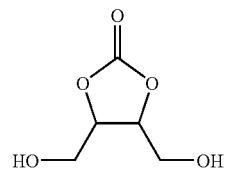

meso-erythrytol carbonate.

14. Process according to claim 1 wherein compound (II) is:

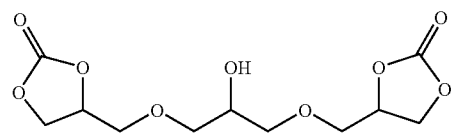

biscarbonate of glycerol diglycidyl ether.

15. An ink jet composition containing a compound obtained by the process according to claim 1.

* * * * *